(12) United States Patent
Knoesche et al.

(10) Patent No.: US 7,488,842 B2
(45) Date of Patent: Feb. 10, 2009

(54) METHOD FOR PRODUCING ISOCYANATES

(75) Inventors: Carsten Knoesche, Niederkirchen (DE); Andreas Woelfert, Bad Rappenau (DE); Andreas Daiss, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 38 days.

(21) Appl. No.: 11/570,408

(22) PCT Filed: Jun. 22, 2005

(86) PCT No.: PCT/EP2005/006745

§ 371 (c)(1),
(2), (4) Date: Dec. 11, 2006

(87) PCT Pub. No.: WO2005/123665

PCT Pub. Date: Dec. 29, 2005

(65) Prior Publication Data

US 2008/0027242 A1    Jan. 31, 2008

(30) Foreign Application Priority Data

Jun. 22, 2004    (DE) ...................... 10 2004 030 164

(51) Int. Cl.
*C07C 263/10*    (2006.01)

(52) U.S. Cl. ..................................... 560/347

(58) Field of Classification Search .................. 560/347
See application file for complete search history.

(56) References Cited

U.S. PATENT DOCUMENTS

| 3,381,025 | A | * | 4/1968 | Mitsumori et al. | .......... 560/347 |
| 5,679,839 | A | | 10/1997 | Armand et al. | |
| 5,756,063 | A | * | 5/1998 | Nuernberg et al. | .......... 423/488 |
| 2004/0068137 | A1 | * | 4/2004 | Herold et al. | ............... 560/347 |

FOREIGN PATENT DOCUMENTS

| DE | 102 45 704 | 4/2004 |
| EP | 0 289 840 | 11/1988 |
| EP | 0 570 799 | 11/1993 |
| EP | 0 593 334 | 4/1994 |
| EP | 0 699 657 | 3/1996 |
| EP | 0 749 958 | 12/1996 |
| EP | 0 928 785 | 7/1999 |

* cited by examiner

*Primary Examiner*—Sikarl A Witherspoon
(74) *Attorney, Agent, or Firm*—Oblon, Spivak, McClelland, Maier & Neustadt, P.C.

(57) ABSTRACT

The invention relates to a process for preparing isocyanates by reacting amines with phosgene in the gas phase in a reaction zone, with the reaction mixture being passed through a zone into which a liquid is sprayed to stop the reaction, wherein the reaction mixture is passed through a zone having a reduced flow cross section between the reaction zone and the zone into which the liquid is sprayed.

27 Claims, No Drawings

METHOD FOR PRODUCING ISOCYANATES

The invention relates to a process for preparing isocyanates in the gas phase. Isocyanates are produced in large quantities and serve mainly as starting materials for the production of polyurethanes. They are usually prepared by reaction of the corresponding amines with phosgene.

One possible way of preparing isocyanates is the reaction in the gas phase. The advantages of this type of process are a reduced phosgene holdup, the avoidance of intermediates which are difficult to phosgenate and increased reaction yields. Apart from effective mixing of the feed streams, achievement of a narrow residence time spectrum and maintenance of a narrow residence time window are important prerequisites for being able to carry out such a process industrially. These requirements can, for example, be satisfied by the use of tube reactors operated under turbulent conditions or by means of flow tubes with internals.

Various processes for preparing isocyanates by reaction of amines with phosgene in the gas phase are known from the prior art.

EP-A-593 334 describes a process for preparing aromatic diisocyanates in the gas phase, in which the reaction of the diamine with phosgene takes place in a tube reactor without moving parts and with a constriction of the walls along the longitudinal axis of the tube reactor. However, the process is problematical since mixing of the feed streams solely by means of a constriction of the walls does not function well compared to use of a correct mixing device. Poor mixing usually leads to undesirably high solids formation.

EP-A-699 657 describes a process for preparing aromatic diisocyanates in the gas phase, in which the reaction of the respective diamine with phosgene takes place in a two-zone reactor in which the first zone making up from 20% to 80% of the total reactor volume is ideally mixed and the second zone making up from 80% to 20% of the total reactor volume has plug flow. However, since at least 20% of the reaction volume is ideally backmixed, a nonuniform residence time distribution results and can lead to undesirably increased solids formation.

EP-A-289 840 describes the preparation of diisocyanates by gas-phase phosgenation, in which the preparation takes place, according to the invention, in a turbulent stream at temperatures of from 200° C. to 600° C. in a cylindrical space without moving parts. The omission of moving parts reduces the risk of loss of containment of phosgene. Due to the turbulent flow in the cylindrical space (tube), a good uniform flow distribution in the tube (if fluid elements close to the wall are discarded) and thus a narrow residence time distribution are achieved, which can lead, as described in EP-A-570 799, to a reduction in solids formation.

EP-A-570 799 relates to a process for preparing aromatic diisocyanates in the gas phase, in which the reaction of the respective diamine with phosgene is carried out in a tube reactor at above the boiling point of the diamine within a mean contact time of from 0.5 to 5 seconds. As described in the document, both excessively long and excessively short reaction times lead to undesirable solids formation. The document therefore discloses a process in which the mean deviation from the mean contact time is less than 6%. Adherence to this contact time is achieved by the reaction being carried out in a stream flowing through a tube which has either a Reynolds number of above 4000 or a Bodenstein number of above 100.

EP-A-749 958 describes a process for preparing triisocyanates by gas-phase phosgenation of (cyclo)aliphatic triamines having three primary amino groups, in which the triamine and phosgene are continuously reacted with one another in a cylindrical reaction space heated to from 200° C. to 600° C. at a flow velocity of at least 3 m/s.

EP-A-928 785 describes the use of microstructure mixers for the phosgenation of amines in the gas phase. A disadvantage of micromixers is that even very small amounts of solid, whose formation cannot be completely ruled out in the synthesis of the isocyanates, can lead to blocking of the mixer, which reduces the time for which the phosgenation plant is available.

However, it is in all cases necessary to stop the reaction effectively after an optimal reaction time in order to prevent the formation of solids by subsequent reactions of the isocyanate.

DE 10245704 A1 describes rapid cooling of a reaction mixture comprising at least an isocyanate, phosgene and hydrogen chloride in a quenching zone. The quenching zone comprises at least 2 nozzle heads which in turn have at least 2 individual nozzles. In the quenching zone, the reaction gas is mixed with the sprayed liquid droplets. Evaporation of the liquid quickly reduces the temperature of the gas mixture, so that the loss of desired isocyanate product as a result of high temperatures is reduced. Furthermore, the nozzle arrangement suppresses early contact of the hot reaction gas with the walls of the quenching zone, so that the formation of deposits on the surfaces is reduced.

A disadvantage of the process described is the quenching times of from 0.2 to 3.0 s, which lead to a significant, avoidable loss of isocyanate.

It was an object of the invention to develop a process for preparing isocyanates in the gas phase, in which the reaction is stopped within a sufficiently short time after the optimal residence time has been attained and simple separation of the isocyanate from the other constituents of the reaction mixture can be achieved.

This object was able to be achieved by carrying out the reaction in a reaction zone and passing the reaction mixture through a zone into which a liquid is sprayed to stop the reaction. In this process, a region having a reduced flow cross section is located between the reaction zone and the zone in which the reaction is stopped.

As reaction zone, it is possible to use tube reactors, flow tubes with or without internals or plate reactors.

The invention accordingly provides a process for preparing isocyanates by reacting amines with phosgene in the gas phase in a reaction zone, with the reaction mixture being passed through a zone into which a liquid is sprayed to stop the reaction, wherein the reaction mixture is passed through a zone having a reduced flow cross section between the reaction zone and the zone into which the liquid is sprayed.

The constriction of the flow cross section is selected so that after leaving the constriction the reaction gas is firstly cooled appreciably and secondly has a high flow velocity which brings about effective secondary atomization of the quenching liquid. Both requirements can be achieved by the mach number of the flow in the constriction being from 0.1 to 1.0, preferably from 0.2 to 1.0, particularly preferably from 0.3 to 1.0. For the present purposes, the mach number is the local flow velocity divided by the local velocity of sound in the reaction mixture. The mach number requirement directly determines the size of the narrowest cross section for a given mass flow. The ratio of flow cross section in the constriction to the flow cross section in the reaction zone is from 1/1.2 to 1/10, preferably from 1/2 to 1/10, particularly preferably from 1/3 to 1/10. The zone into which a liquid is injected will hereinafter also be referred to as the quenching zone, and the spraying-in of the liquid will be referred to as quenching.

In this quenching zone, the reaction mixture which consists essentially of the isocyanates, phosgene and hydrogen chloride is intensively mixed with the liquid sprayed in. Mixing is carried out so that the temperature of the reaction mixture is reduced by from 50 to 300° C., preferably from 100 to 250° C., from an initial temperature in the range from 250 to 500° C. and the isocyanate present in the reaction mixture goes over completely or partly into the sprayed-in liquid droplets as a result of condensation, while the phosgene and the hydrogen chloride remain essentially completely in the gas phase.

The proportion of the isocyanate present in the gaseous reaction mixture which goes over into the liquid phase in the quenching zone is preferably from 20 to 100% by weight, particularly preferably from 50 to 100% by weight and in particular from 70 to 100% by weight, based on the isocyanate present in the reaction mixture.

The reaction mixture preferably flows through the quenching zone from the top downward. Below the quenching zone, there is a collection vessel in which the liquid phase is precipitated, collected and removed from the reaction space via an outlet and subsequently worked up. The gas phase which remains is removed from the reaction space via a second outlet and is likewise worked up.

The liquid droplets are produced by means of single- or two-fluid atomizer nozzles, preferably single-fluid atomizer nozzles, and preferably have a Sauter diameter $d_{23}$ of from 5 to 5000 μm, particularly preferably from 5 to 500 μm and in particular from 5 to 250 μm. The Sauter diameter $d_{23}$ describes the ratio of droplet volume to droplet surface area except for a constant factor (K. Schwister: Taschenbuch der Verfahrenstechnik, Fachbuchverlag Leipzig, Carl Hanser Veriag 2003) and is thus the parameter of the droplet size distribution produced which is relevant to the quenching process.

The atomizer nozzles produce, depending on the design, a spray cone angle of from 10 to 140°, preferably from 10 to 120°, particularly preferably from 10° to 100°.

According to the invention, a constriction in the cross section is located between the reaction zone and the quenching zone and effects depressurization of the gas, accompanied by a reduction in the concentration of the reactants and a first decrease in the temperature of the reaction gas. Furthermore, the reaction gas stream leaving the constriction in the cross section at a very high velocity brings about secondary atomization of the quenching liquid when it meets the quenching liquid spray, so that the spray has a particularly large specific surface area. Owing to the large specific surface area and the high relative velocity between reaction gas and quenching liquid, mass transfer and heat transfer between reaction gas and quenching liquid are increased. This greatly reduces the contact times necessary for cooling of the reaction mixture and minimizes the loss of desired isocyanate product as a result of further reaction to form by-products.

The free flow cross section in the quenching zone is, based on the free flow cross section in the reaction zone, from 5/1 to 1/2, preferably from 4/1 to 1/1, particularly preferably from 3/1 to 1/1.

The liquid which is sprayed in through the atomizer nozzles has to have a good solvent capability for isocyanates. Preference is given to using organic solvents. In particular, use is made of aromatic solvents which may be substituted by halogen atoms. Examples of such liquids are toluene, benzene, nitrobenzene, anisole, chlorobenzene, dichlorobenzene (ortho, para), trichlorobenzene, xylene, hexane, diethyl isophthalate (DEIP), tetrahydrofuran (THF), dimethylformamide (DMF) and mixtures thereof.

In a preferred embodiment of the process of the invention, the liquid sprayed in is a mixture of isocyanates, a mixture of isocyanates and solvent or an isocyanate, with proportions of low boilers such as HCl and phosgene being able to be present in the quenching liquid used. Preference is given to using the isocyanate which is prepared in the respective process. Since the reaction ceases as a result of the temperature drop in the quenching zone, secondary reactions with the isocyanates sprayed in can be ruled out. The advantage of this embodiment is, in particular, that it is not necessary to separate off the solvent.

The temperature of the liquid sprayed in is preferably from 0 to 300° C., particularly preferably from 50 to 250° C. and in particular from 70 to 200° C., so that the desired cooling and condensation of the isocyanate is achieved by means of the amount of liquid sprayed in.

The velocity of the reaction gas in the quenching zone is preferably greater than 1 m/s, particularly preferably greater than 10 m/s and in particular greater than 20 m/s.

To achieve rapid cooling of the gaseous reaction mixture in the quenching zone and rapid conversion of the isocyanate into the liquid phase, the droplets of the liquid sprayed in have to be very quickly distributed finely over the entire flow cross section of the reaction gas. The desired temperature decrease and the desired transfer of the isocyanate into the droplets is preferably carried out in from $10^{-4}$ to 10 seconds, particularly preferably in $5 \times 10^{-4}$ to 1 second and in particular in from 0.001 to 0.2 second. The above times are defined as the period of time between entry of the reaction gas into the quenching region and the point in time at which the reaction gas is 10% away from the adiabatic final temperature of the mixture of reaction gas and droplets. The selected periods of time make it possible to avoid a loss of isocyanate as a result of secondary or further reactions virtually completely.

The mass ratio of the amount of liquid sprayed in to the amount of gaseous reaction mixture is preferably from 100:1 to 1:10, particularly preferably from 50:1 to 1:5 and in particular from 10:1 to 1:2.

The reaction of the amine with phosgene in the gas phase can be carried out under known conditions.

Mixing of the reaction components amine and phosgene can occur before or in the reactor. It is thus possible to install a mixing unit, for example a nozzle, upstream of the reactor so that a premixed gas stream comprising phosgene and amine is introduced into the reactor.

In one embodiment of the process of the invention, the phosgene stream is distributed very uniformly over the entire width of the reactor by means of a distributor element. The amine stream is fed in at the beginning of the reactor where a distributor channel provided with holes or mixing nozzles is installed in the reaction channel and preferably extends over the entire width of the reactor. The amine, if appropriate mixed with an inert medium, is fed through the holes or mixing nozzles into the phosgene stream.

The inert medium is a medium which is gaseous at the reaction temperature and does not react with the starting materials. For example, nitrogen, noble gases such as helium or argon or aromatics such as chlorobenzene, dichlorobenzene or xylene can be used. Preference is given to using nitrogen as inert medium.

In the process of the invention, it is possible to use primary amines which can preferably be converted into the gas phase with decomposition. Amines, in particular diamines, based on aliphatic or cycloaliphatic hydrocarbons having from 1 to 15 carbon atoms are particularly useful here. Examples are 1,6-diaminohexane, 1-amino-3,3,5-trimethyl-5-aminomethylcyclohexane (IPDA) and 4,4'-diaminodicyclohexylmethane. Preference is given to using 1,6-diaminohexane (HDA).

The process of the invention can also be carried out using aromatic amines which can preferably be converted into the gas phase without decomposition. Examples of preferred aromatic amines are toluenediamine (TDA), preferably the 2,4 or 2,6 isomers or mixtures thereof, diaminobenzene, naphthylenediamine (NDA) and 2,4'- or 4,4'-methylene(diphenylamine) (MDA) or isomer mixtures thereof.

In the process of the invention, it is advantageous to use phosgene in an excess over the amino groups. The molar ratio of phosgene to amino groups is usually from 1.1:1 to 20:1, preferably from 1.2:1 to 5:1.

To carry out the process of the invention, it can be advantageous to preheat the streams of reactants prior to mixing, usually to temperatures of from 100 to 600° C., preferably from 200 to 500° C. The reaction in the reaction channel usually takes place at a temperature of from 150 to 600° C., preferably from 250 to 500° C. The process of the invention is preferably carried out continuously.

In a preferred embodiment, the dimensions of the reactor and the flow velocities are such that turbulent flow, i.e. flow with a Reynolds number of at least 2300, preferably at least 2700, is present, with the Reynolds number being formed with the hydraulic diameter of the reactor. The Reynolds number determines the flow regime and thus the residence time distribution in the reaction tube (H. Schlichting: Grenzschichttheorie, Verlag G. Braun, 1982; M. Baerns: Chemische Reaktionstechnik, Georg Thieme Verlag Stuttgart, 1992). The gaseous reactants preferably pass through the reactor at a flow velocity of from 20 to 150 meters/second, preferably from 30 to 100 meters/second.

In general, the mean contact time in the process of the invention is from 0.05 to 5 seconds, preferably from 0.06 to 1 second, particularly preferably from 0.1 to 0.45 second. For the purposes of the present invention, the mean contact time is the period of time from commencement of mixing of the starting materials to termination of the reaction by means of the quench. In a preferred embodiment, the flow in the process of the invention is characterized by a Bodenstein number of greater than 10, preferably greater than 100 and particularly preferably greater than 500. The Bodenstein number is a measure of the degree of backmixing in the flow apparatus. As the Bodenstein number increases, the backmixing decreases (M. Baerns: Chemische Reaktionstechnik, Georg Thieme Verlag Stuttgart, 1992)

As indicated above, a quenching zone is located at the end of the reactor, which can be a tube reactor, flow tube with internals or plate reactor operated under turbulent conditions. The liquid phase taken from the quenching zone and the gas phase are worked up. When a solvent is used as atomized liquid, a separation of isocyanate and solvent is carried out, usually by means of distillation. The gas phase, which consists essentially of phosgene, hydrogen chloride and possibly unreacted isocyanate, can likewise be separated into its constituents, preferably by distillation or adsorption, and the phosgene can be returned to the reaction and the hydrogen chloride can be utilized either for further chemical reactions, be processed further to hydrochloric acid or be redissociated into chlorine and hydrogen.

The invention is illustrated by the following example.

EXAMPLE 1

67.5 kg/h of reaction gas comprising tolylene diisocyanate isomers, phosgene and hydrochloric acid were produced in a tube reactor (diameter: 8 mm) with upstream mixing device. The reaction gas was then conveyed via a constriction of the cross section having a diameter of 3.0 mm to the quenching zone. The mach number in the narrowest cross section was about 0.85. Two individual single-fluid nozzles having a spray cone opening angle of 80° were located in the quenching zone. The nozzles produced droplets having a Sauter diameter of about 100 μm. The amount of liquid sprayed in was 100 kg/h. The quenching liquid sprayed in consisted of monochlorobenzene. The temperature of the reaction gas on entering the quenching zone was 363° C. and the pressure of the gas was 6.8 bar. The entry temperature of the quenching liquid was 100° C., and the exit velocity of the liquid droplets from the spray nozzle was about 50 m/s. The residence time of the reaction gas in the quenching zone was about 0.01 second. The temperature of the quenched gas dropped to 156° C. in the quenching zone. The desired temperature decrease thus occurred in less than 0.01 second. The amount of tolylene diisocyanate in the reaction gas mixture decreased by 80% relative to the concentration on entering the quenching zone.

The invention claimed is:

1. A process for preparing isocyanates by reacting amines with phosgene in the gas phase in a reaction zone, with the reaction mixture being passed through a zone into which a liquid having a good solvent capability for isocyanates is sprayed to stop the reaction, wherein the reaction mixture is passed through a zone having a reduced flow cross section between the reaction zone and the zone into which the liquid is sprayed.

2. The process according to claim 1, wherein tube reactors, flow tubes with or without internals or plate reactors are used as reaction zone.

3. The process according to claim 1, wherein the ratio of the flow cross section in the constriction to the flow cross section in the reaction zone is from 1/1.2 to 1/10.

4. The process according to claim 1, wherein the ratio of the flow cross section in the constriction to the flow cross section in the reaction zone is from 1/2 to 1/10.

5. The process according to claim 1, wherein the ratio of the flow cross section in the constriction to the flow cross section in the reaction zone is from 1/3 to 1/10.

6. The process according to claim 1, wherein the liquid droplets sprayed in have a Sauter diameter of from 5 to 5000 μm.

7. The process according to claim 1, wherein the liquid droplets sprayed in have a Sauter diameter of from 5 to 500 μm.

8. The process according to claim 1, wherein the liquid droplets sprayed in have a Sauter diameter of from 5 to 250 μm.

9. The process according to claim 1, wherein the temperature of the liquid sprayed in is from 0 to 300° C.

10. The process according to claim 1, wherein the temperature of the liquid sprayed in is from 50 to 250° C.

11. The process according to claim 1, wherein the temperature of the liquid sprayed in is from 70 to 200° C.

12. The process according to claim 1, wherein the liquid sprayed in comprises an organic solvent.

13. The process according to claim 1, wherein the liquid sprayed in comprises an aromatic solvent which may be substituted by halogen atoms.

14. The process according to claim 1, wherein the liquid sprayed in comprises an isocyanate.

15. The process according to claim 1, wherein the liquid sprayed in comprises toluene.

16. The process according to claim 1, wherein the liquid sprayed in comprises benzene.

17. The process according to claim 1, wherein the liquid sprayed in comprises nitrobenzene.

18. The process according to claim 1, wherein the liquid sprayed in comprises anisole.

19. The process according to claim 1, wherein the liquid sprayed in comprises chlorobenzene.

20. The process according to claim 1, wherein the liquid sprayed in comprises ortho-dichlorobenzene.

21. The process according to claim 1, wherein the liquid sprayed in comprises para-dichlorobenzene.

22. The process according to claim 1, wherein the liquid sprayed in comprises trichlorobenzene.

23. The process according to claim 1, wherein the liquid sprayed in comprises xylene.

24. The process according to claim 1, wherein the liquid sprayed in comprises hexane.

25. The process according to claim 1, wherein the liquid sprayed in comprises diethyl isophthalate.

26. The process according to claim 1, wherein the liquid sprayed in comprises tetrahydrofuran.

27. The process according to claim 1, wherein the liquid sprayed in comprises dimethylformamide.

* * * * *